(12) United States Patent  
Moore et al.

(10) Patent No.: US 6,548,309 B1  
(45) Date of Patent: Apr. 15, 2003

(54) PROCEDURE FOR ASSAY OF LIQUIDS CONTAINING UNDISSOLVED SOLIDS, SEMISOLIDS OR COLLOIDS

(75) Inventors: Norman James Moore, North Berwick, ME (US); Vincent Anthony Sy, Cumberland Center, ME (US)

(73) Assignee: Binax, Inc., Portland, ME (US)

( * ) Notice: Subject to any disclaimer, the term of this patent is extended or adjusted under 35 U.S.C. 154(b) by 0 days.

(21) Appl. No.: 09/044,677

(22) Filed: Mar. 19, 1998

(51) Int. Cl.[7] ............................................. G01N 33/553
(52) U.S. Cl. ...................... 436/500; 436/510; 436/524; 436/528; 436/530; 436/20; 436/21; 436/808; 436/814; 436/818; 436/825; 436/514; 435/4; 435/7.37; 435/12; 435/30; 435/32; 435/34; 435/38; 604/1
(58) Field of Search ................. 436/500, 510, 436/524, 528, 530, 20, 21, 808, 814, 818, 825, 514; 435/4, 7.37, 12, 30, 32, 34, 38; 604/1

(56) References Cited

U.S. PATENT DOCUMENTS

| | | | | |
|---|---|---|---|---|
| 4,094,647 A | * | 6/1978 | Deutsch et al. ............... 23/253 |
| 4,703,017 A | * | 10/1987 | Campbell et al. ............ 436/501 |
| 4,789,639 A | * | 12/1988 | Fleming ....................... 436/178 |
| 4,857,453 A | * | 8/1989 | Ullman et al. .................. 435/7 |
| 4,861,711 A | * | 8/1989 | Friesen et al. ............... 436/514 |
| 4,963,325 A | * | 10/1990 | Lennon et al. ................. 422/61 |
| 5,000,193 A | * | 3/1991 | Heelis et al. ................ 128/760 |
| 5,006,474 A | * | 4/1991 | Horstman et al. ............ 436/524 |
| 5,091,316 A | * | 2/1992 | Monthony et al. ........... 435/295 |
| 5,163,441 A | * | 11/1992 | Monthony et al. ........... 128/759 |
| 5,169,789 A | * | 12/1992 | Bernstein ..................... 436/501 |
| 5,250,412 A | * | 10/1993 | Giegel .......................... 435/7.1 |
| 5,260,221 A | * | 11/1993 | Ramel et al. ................ 436/169 |
| 5,266,266 A | * | 11/1993 | Nason ........................... 422/58 |
| 5,314,855 A | * | 5/1994 | Thorpe et al. ................. 502/80 |
| 5,360,605 A | * | 11/1994 | Shanbrom ................. 424/78.08 |
| 5,415,994 A | * | 5/1995 | Imrich et al. ..................... 435/5 |
| 5,425,915 A | * | 6/1995 | Phillips et al. ................. 422/58 |
| 5,622,871 A | * | 4/1997 | May et al. .................... 436/514 |
| 5,714,389 A | | 2/1998 | Charlton et al. |
| 5,766,962 A | * | 6/1998 | Childs et al. ................ 436/518 |
| 5,869,345 A | * | 2/1999 | Chandler ..................... 436/514 |
| 5,935,804 A | * | 8/1999 | Laine et al. ................... 435/18 |

\* cited by examiner

Primary Examiner—Christopher L. Chin  
Assistant Examiner—Pensee T. Do  
(74) Attorney, Agent, or Firm—Mary Helen Sears

(57) ABSTRACT

In qualitative or quantitative assays which employ a test device comprising a test strip pretreated for detection of a specified target analyte dissolved in a liquid medium, the presence of solid, semisolid and/or colloidal materials in the liquid medium may interfere with the assay results. The present invention involves collecting the sample from a flowing or quiescent pool of liquid also containing solid, semisolid or colloidal material with a swab comprised of a handle and a mass of fibrous material or foamed, open cell material which, when immersed in and thoroughly wetted by the liquid, entraps solid, semisolid and/or colloidal material and delivers only the liquid to the sample receiving zone of the test strip.

12 Claims, 1 Drawing Sheet

PROCEDURE FOR ASSAY OF LIQUIDS CONTAINING UNDISSOLVED SOLIDS, SEMISOLIDS OR COLLOIDS

BACKGROUND OF THE INVENTION

This invention relates to an improvement in rapid and highly sensitive assays for ligands contained, or suspected of being contained, in liquids of non-uniform character in which solid particles and/or other undissolved substances of a semisolid or colloidal nature that are likely to interfere with or obscure the result of the assay typically are also present. Such liquids include, e.g., blood, urine, lymph, lacteal fluid, and like biological liquids and liquids that have been deliberately constituted such as inoculated bacterial media, dilutions thereof, dilutions of biological samples, etc., and non-biological liquids that contain solids, semisolids or colloids as collected such as groundwater and other environmental samples, sea water, surface water, potable water, liquid from heating, ventilation and air conditioning systems, waste water and like liquids. The assay may be an immunoassay performed in a disposable solid state device comprising a suitably housed test strip which is in turn comprised of sorbent material and which defines a flow path along which the liquid test sample travels to a test site impregnated with a conjugate of (1) a binding partner for the ligand sought to be detected, and (2) a particulate material that produces visible color in the presence of the ligand. The improvements achieved by using this invention can also be beneficially realized in assays other than immunoassays, such as receptor or molecular probe assays.

A test device suitable for immunoassay may be so constituted that it performs the assay in either the sandwich or the competition mode. Such a test device is often constructed so as to yield a quantitative result for the ligand, but it may also be designed and constructed so as to furnish only a positive or negative answer concerning the presence of the ligand. Its flow path may be designed for unidirectional or bidirectional flow of components.

The assay in which the benefits of this invention are realizable must be extremely sensitive, so that it is able to detect very low concentrations of ligand in the test fluid accurately—i.e., without producing the false positive or false negative results often experienced when using both currently sold disposable solid state devices and prior art assay methods which required multiple dilutions of the biological fluid. The latter assays in the prior art often employed, e.g., "dipstick" type devices and the like and required relatively long incubation times for reaction of the ligand with its labeled binding partner. Obviously because the test fluids referred to above typically contain solid and semisolid particles and/or other undissolved components such as fats and other colloidal substances that may interfere with or obscure the result of an assay for a particular dissolved ligand, it is important to provide for removal of these potential interferants prior to the performance of the assay itself.

U.S. Pat. No. 5,714,389 issued Feb. 3, 1998 to Charlton et al. describes assays performable on bodily fluids containing solid particulate material using specially constructed test devices which are adapted to be dipped directly into the fluid. In these devices the sample flow path is constructed so as to include, near its ingress, a filtration means having the purpose to trap particulate components of the liquid test sample as that sample flows toward the test site. The patent alleges that the inclusion of this filtration means contributes to the sensitivity and accuracy of the test, and especially to the low incidence of false positives, including borderline false positives, observed from its use.

An important object of the present invention is to achieve all of the advantages of the test system disclosed in the Charlton et al. patent, including sensitivity and rapidity of the assay, low incidence of false positives and ability to yield reliable results even in the hands of untrained personnel, without experiencing the disadvantages of the specific test device therein described. In particular, an object of this invention is avoidance of the need for directly dipping the test device into the biological test fluid, coupled with avoidance of the need for interposing a filtration means in the flow path of the sample. By dispensing with such a filtration means, one avoids problems that are experienced in instances where the filter means becomes at least partially clogged, or even wholly clogged, by solid, semisolid and/or colloidal particles contained in the test fluid, making it necessary to discard the device without obtaining any useful assay result.

Another important object of this invention is to improve the reliability of delivery to an assay system that will benefit therefrom, whether of the immunoassay, molecular probe assay, receptor assay or some other assay type, of a relatively constant and reproducible sample volume to the test device.

SUMMARY OF THE INVENTION

The invention involves the use of a swab which contacts the test sample by immersion therein so that it is wetted, and preferably saturated, with the test sample liquid. The wetted swab is then removed from the sample and applied to a test device. In immunoassay applications, the sample applied to the test device is placed in contact with a test strip which has been designed and constructed to assay specifically for a particular ligand suspected of being present in the test liquid. The swab entraps solid and semisolid particulate matter and other undissolved matter such as fats and other colloidal material contained in the test sample and delivers only the liquid portion of the sample which is to be assayed into contact with the test strip. Typically, the sample then moves along a flow path, reacting with a binding partner that has been conjugated to a label. In cases where the test sample is, e.g., urine, many known test devices for home use require the user to contact the device with a urine stream. According to the present invention, the user will be instructed to contact the swab (which is supplied firmly attached to a handle) with the urine stream and then apply the swab to the sample device. Use of the swab thus eliminates all risk of device contamination with unrelated substances; it also minimizes the potential for contact of the urine by the user's hands.

Preferably the swab is formed of a loose, fluffy fibrous material but other fibrous materials and certain open-pore materials, such as foamed resins and rubbers and sponges can also be used. Closed-cell materials that lack fibrous structure, however, are unsuitable for the swabs used in this invention. Swabs have been widely used heretofore to apply medicaments, to dry exposed surface areas of an inanimate object or a mammalian body, or to collect a small specimen of material to be viewed or further treated by moving the swab across a surface—e.g., the "throat swab" referred to in Example 1 of application Ser. No. 07/706,639 now U.S. Pat. No. 6,168,956 of Howard Chandler, assigned to SmithKline Diagnostics, Inc., but exclusively licensed in a wide area of applications to Binax, Inc., the intended assignee of the present application. Swabs have also been used heretofore to collect solid or semisolid samples in small quantities—e.g., phlegm, sputum, nasal discharge, etc.—for microscopic viewing or transfer to another receptacle for further processing.

According to this invention, the swab is to be immersed in the liquid sample, whereby liquid is sorbed by it and solid, semisolid and colloidal particles either cling to it or are left behind in the liquid. In contrast, swabs have been used in the past to collect samples by moving them across a semi-dry surface (such as the back of a patient's throat) or touching them to a mass of semisolid matter. In this invention, when the swab, after immersion in the test liquid, is deposited in a partially covered swab well in accordance with this invention as hereinafter more fully described, the absorbed liquid sample is largely expelled, but the entrained solids, semisolids and colloids that cling to a fibrous swab surface or become trapped in the open-pore structure of a suitable non-fibrous swab are retained in or on the swab structure. While different types of swabs may vary somewhat in their capacity to absorb liquid upon immersion therein—i.e., a cotton or Dacron swab and a sponge may have slightly different absorptive capacities—any given swab type of relatively uniform size has been found to absorb and to deliver to the test device an essentially uniform volume of liquid sample. By contrast, a pipette is not only easily clogged by solid, semisolid or colloidal substances, but in instances where the clogging is only partial, it may be hard to judge the liquid sample volume delivered to a test device, making it difficult in some cases to compare what should be duplicate results from a given test liquid. A similar problem, of course, plagues devices adapted to be dipped directly into the test sample and this problem exists whether or not the device is equipped with a filter means in the sample flow path as described in U.S. Pat. No. 5,714,389.

A test device preferably used for immunoassay in conjunction with the use of this invention is an immunochromatographic device of the type disclosed in application Ser. No.07/706,639 of Howard M. Chandler filed May 29, 1991, having two opposable, preferably hinged, halves wherein one half contains a sample well or sample pad and the other half carries the test strip comprising a flow path and test site and the liquid test sample is applied to the flow path by bringing the halves of the device into closed contact. This device can be adapted for use in a unidirectional or bidirectional flow assay format as therein disclosed; in either case, the improvement provided by the present invention can be readily utilized. The device may be specifically adapted to perform a sandwich or a competitive immuno-assay. It may also be specifically adapted to provide either a qualitative or a quantitative result.

Other immunoassay test devices wherein liquid sample is caused to move from the inlet end of a test strip along a flow path by means of capillary action, wicking, sorption or any other mechanism effective to create flow of sample along the strip have been described in the art and may also be readily adapted to receive a swab that has been wetted with test sample by immersion therein to apply test liquid therefrom to a test strip that has been suitably prepared to assay the test sample for the particular ligand to be determined. Examples of such immuno-assay devices include that disclosed by Charlton et al., which could readily be so modified and that disclosed, e.g., in May et al. U.S. Pat. No. 5,622,871 issued Apr. 22, 1997, which likewise could be readily adapted to receive a swab previously immersed in a test sample that performs the dual function of applying liquid test sample to the flow path and filtering out solid particles and other undissolved substances which might potentially interfere with the assay.

Among the ligands which can successfully be assayed for using this method are bacteria such as *E. coli*, various lower respiratory tract organisms such as those that cause pneumonia, e.g., Streptococcus or Legionella, various upper respiratory tract organisms such as Hemophilus and those that cause influenza-like syndromes, sexually transmitted bacteria such as those that cause gonorrhea, antigens such as human chorionic gonadotropin (hCG), spermatozoa antigens, human luteinizing hormone, progesterone and estrogen. Other suitable ligands detectable by this method will readily occur to those skilled in the art.

The immunoassay may be of the "sandwich" or the "competitive" type, depending upon the particular ligand to be assayed for. In all cases, it is performed in a manner that is generally described in the art, e.g., in application Ser. No. 07/706,939 and in various patents such as those of Charlton et al. and May et al. cited hereinabove. The other types of assays, such as receptor and molecular probe assays, to which the invention is applicable, may likewise be configured in various formats, all of which can readily be adapted to receive sample delivered by a swab.

DETAILED DESCRIPTION OF THE INVENTION

Figure 1:
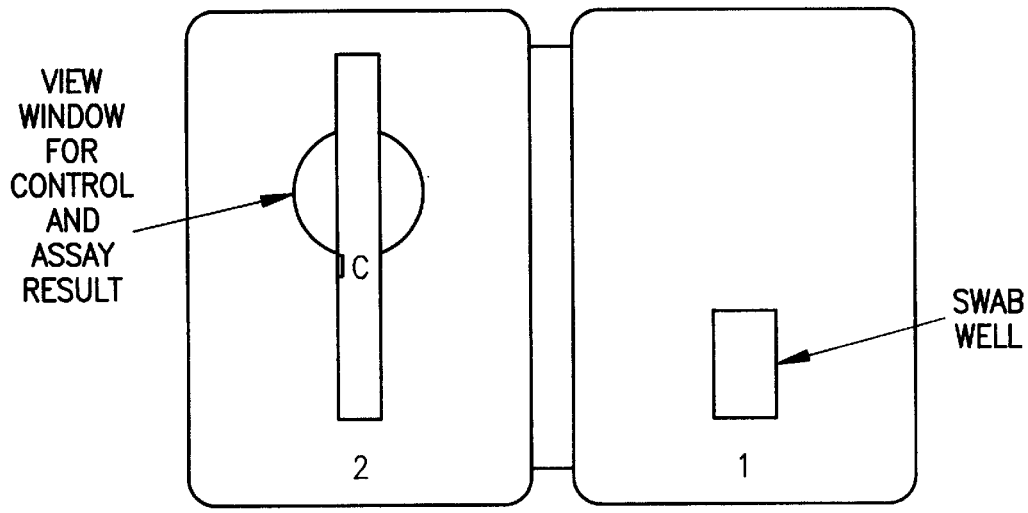
FIG. 1 is a view of a hinged device of the type disclosed in application Ser. No. 07/706,639 now U.S. Pat. No. 6,168,956 showing the relative locations of the swab well, the test strip and the window for viewing the result of the test and its control. This device is specifically discussed in Example 1.

The present invention constitutes an improvement in known methods for conducting various forms of assays, as already noted. It is explained herein and exemplified by reference to its use in a device for the conduct of sandwich or competitive immunoassays which is adapted for a single use and is disposable. Devices of this type are each designed to assay for a preselected ligand. The use of the invention enables untrained personnel to conduct an immunoassay on a non-uniform liquid sample in which is present solid, semisolid and/or colloidal substances that may interfere with, obscure the results of, or otherwise undesirably affect the assay. The specific examples of test devices and associated procedures hereinafter described and other similar examples of devices and procedures that will readily occur to those skilled in this art are accordingly well-adapted for inclusion in immunoassay test kits sold over-the-counter which may be used in the home as well as in doctors' offices, clinics, hospitals, etc., for rapid diagnosis of pregnancy, venereal diseases, respiratory diseases such as pneumonia, Legionnaires Disease, Streptococcus infections, *E. coli* contamination and other conditions which result in the presence of a dissolved antigenic substance in a fluid that is non-homogenous because of the presence of undissolved solids, semisolids and/or colloids. Test kits containing test devices of the immunoassay or other type (such as receptor assays and probe assays) may, in some instances, be utilized to monitor drug dosage levels, the efficacy of treatment for a given disease or infection, etc. Suitably constructed test kits may also be used to test certain foods for the presence of specific bacteria, to test samples for environmentally undesirable contaminants and for a variety of other purposes well known in the art.

Broadly speaking, the improvement which constitutes the present invention can be applied to any assay wherein it is desired to achieve direct detection or quantification of a specific dissolved ligand suspected of being present in a liquid that also contains undissolved solid, semisolid and/or colloidal substances that may interfere with or obscure the assay result.

While the use of this improvement in lieu of placing a filtration means in the flow path of a test device is specifically exemplified herein with reference to the general category of immunoassay device disclosed and claimed in U.S. Pat. No. 6,168,956 it is to be understood that any of the disposable immunoassay test devices in now on the market and any of those described in the literature, including patents, can easily be adapted to the use of this invention by those of ordinary skill in immunoassay technology. In addition, devices adapted for other types of assays, including particularly receptor assays and molecular probe assays, can likewise readily be adapted by those of ordinary skill in those assays to the use of this invention.

Because the use of a given swab of the same size and material allows unskilled personnel to deliver an essentially constant volume of liquid sample to the test device (unlike the use of pipettes and immersible test devices), such use may even expand the universe of performability of some assays and its use will certainly contribute to the reliability of some assays now being performed by unskilled personnel.

EXAMPLE 1

Legionella Assay

Figures 1A, 1B:
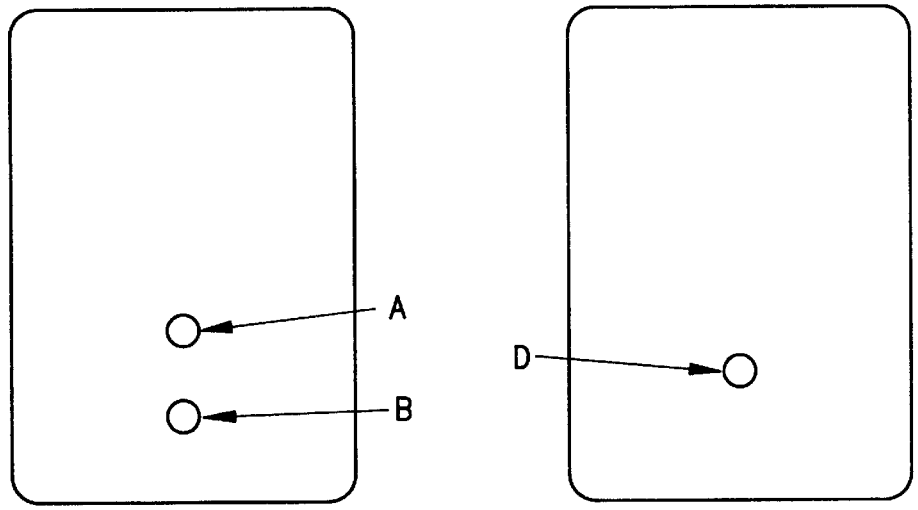
FIG. 1A is a representation of the overlayer for the right-hand side of the FIG. 1 device as described in Example 1.
FIG. 1B is a representation of the overlayer for the left-hand side of the FIG. 1 device as described in Example 1.

A. Test Device Preparation:

A test device comprising a hinged desiccated cardboard housing equipped with a plastic window so placed as to allow viewing of both the sample result and the control result at the end of the assay is prepared with the configuration of FIG. 1 hereof. The device has a recess into which is placed a preformed plastic swab well for receiving the sample-wetted swab on the right-hand side (labeled 1 in the drawing). An overlabel shown in FIG. 1A is then placed over the entire right-hand side of the device. The overlabel has been equipped, with two holes—a lower one (marked B on FIG. 1A) into which the saturated swab is to be inserted and an upper one (marked A on FIG. 1A) toward which the swab will be pushed after insertion thereof into hole B. The arrangement of the overlabel with its holes A and B, and the swab well cooperate to hold the swab in a proper position during the assay and to promote the expulsion of sorbed liquid from the swab.

A longer preformed plastic well is glued at its bottom to the left-hand side of the device (labeled 2 in FIG. 1) and a preassembled test strip (marked C on FIG. 1) described below, is inserted into this well and held in place by an adhesive applied to the bottom thereof. An overlabel shown in FIG. 1B is placed atop the left-hand side. It has been equipped with a single hole (marked D in FIG. 1B) which mates to right-hand side hole A when the device is closed for performance of the assay.

The assembled device is stored in a sealed pouch with desiccant until it is used. Prior to sealing the pouch and storing, a lightly adhesive strippable tape is placed on the outer edge of the right-hand half of the device.

B. Test Strip Preparation and Construction

Figure 1C:
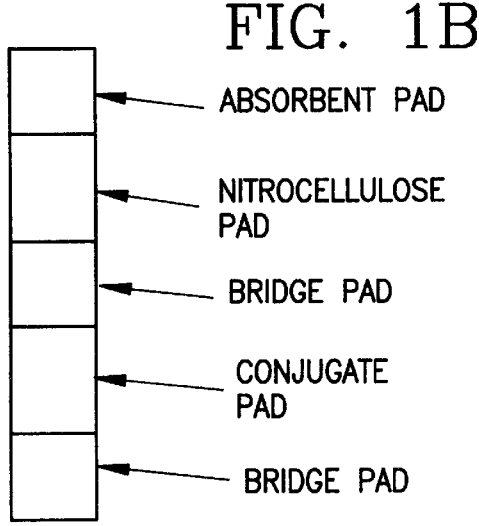
FIG. 1C is a sketch of the test strip of the FIG. 1 device showing the relative locations and relationships of the various pads which make up that strip.

As FIG. 1C shows, the test strip for the Legionella assay is comprised of a first bridge pad of sorbent material which contacts another pad of sorbent material which has been impregnated with a conjugate of gold particles and affinity-purified rabbit anti-Legionella anti-bodies. In use, this conjugate is rendered flowable by contact with the liquid sample. The conjugate pad in turn contacts a second bridge pad of sorbent material through which the sample and conjugate flow into a nitrocellulose pad on which a capture line for sample that has reacted with gold conjugate has been established by imbedding affinity-purified rabbit anti-Legionella antibodies therein. The nitrocellulose pad also includes a downstream control line established by striping the pad with goat anti-rabbit immunoglobulin (IgG). After passing the nitrocellulose pad, the sample residue passes to an absorbent pad which serves as a reservoir for liquid.

The bridge pads are of cellulose (Ahlstrom, 1281) and they are used directly without special treatment.

The conjugate pad is of non-woven polyester; in preparing the pad for use in this assay, gold particles of 45 nm. diameter are conjugated, according to the method of J. DeMey, "The Preparation and Use of Gold Probes" in *Immuno-chemistry: Modern Methods and Applications* (J. M. Polak and S. Van Noorden, eds., Wright, Bristol, England, 1986) or any of various other known methods, to affinity-purified anti-Legionella antibodies. The affinity-purification is achieved as described by P. Tyssen, "Affinity Chromatography of Immuno-globulins or Antibodies" contained in *Practice and Theory of Enzyme Immunoassays* (R. H. Burdon and P. H. Van Knippenberg, eds., Elsevier, N.Y., 1985). The gold conjugate particles are mixed with drying agent and embedded into a conjugate pad. The drying agent used is aqueous 5 mM sodium tetraborate of pH 8.0 containing 1.0 percent bovine serum albumin, 0.1 percent Triton X-100, 2.0 percent Tween-20, 6.0 percent sucrose and 0.02 percent sodium azide. The pad is heated sufficiently to remove all liquid present and stored in a low humidity environment pending assembly of the test device. This pad is especially chosen to hold the dry conjugate and to release it when wetted by the sample.

The nitrocellulose pad is first treated by embedding affinity-purified rabbit anti-Legionella antibodies (purified by the method of P. Tyssen identified above) into a first portion of the pad. These antibodies act as the capture line. In a second portion of the pad which is downstream of the first portion when the test device is used, a control line is established by striping goat anti-rabbit IgG on the surface of the pad. The nitrocellulose is then desiccated at a temperature of 18–25° C. to promote permanent protein absorption thereto. The nitrocellulose is then blocked by spraying thereon a solution of 0.2 percent meta-soluble zein in 20 mM sodium phosphate (pH 7.8). The blocking serves to increase the flow rate of sample through the pad and to decrease background effects. The heat desiccation step is then repeated and this pad is stored under low humidity conditions pending assembly of the test strip.

The absorbent pad used is of cellulosic material sold in commerce as Ahlstrom 939. It requires no special treatment. All of the pads are assembled, in the order stated above, on an adhesive strip when the test device is put together for delivery to a customer.

C. Immunoassay Procedure

In the conduct of the assay according to this invention, finished test devices having the swab well, the overlayers with holes and the test strip arranged as shown in the Figures are utilized. A swab fashioned from fibrous cotton is briefly immersed in the urine sample and is then removed from the sample and immediately inserted, through overlayer hole B on the right-hand side of the device, into the sample well of the test device. Two drops of "Reagent A", in this instance a solution of 2.0 percent Tween 20, 0.05 percent sodium azide and 0.5 molar sodium dodecyl sulfate in a 0.05 molar sodium citrate-sodium phosphate buffer of pH 6.5 are added to the sample through the same hole. The adhesive strip on the edge of the right-hand side is peeled away and the device is thereupon closed. The sample immediately contacts the first bridge pad and flows through the immunochromatographic test strip. After 15 minutes, the test sample window and the control window are viewed and the results noted.

D. Comparison of Legionella Test of the Invention with Prior Art Test

Sixty urine samples were collected and stored for 18 to 400 hours to encourage precipitation. Each of the samples exhibited 0 to 50 percent of the total volume of visible precipitated material at the time of analysis. Each sample was analyzed according to two protocols: i.e., that of the present invention and that of the prior art, called "forward flow" herein. For the forward flow method, test devices are utilized which differ from those of this invention in the following respects:

1. Forward flow test devices have a sample pad which is of the same cellulose material as the first bridge pad in the test device in which this invention is exemplified. The sample pad is located on the right-hand side of the device (where the sample well is placed in the device exemplifying the use of the invention). The urine sample is obtained in and applied from a pipette to the sample pad.

2. On the left-hand side of the device, the first bridge pad is omitted in a forward flow device and the gold conjugate pad is so placed that it directly contacts the sample pad when the device is closed. Also in forward flow, two drops of Reagent A, the Tween 20/sodium azide/sodium dodecyl sulfate buffer solution mentioned above, is applied directly to the conjugate pad instead of being added to the urine sample. In all other respects the forward flow test device and method are the same as those described for the device in which the method of this invention is exemplified.

The results of testing all of the 60 urine samples in both modes were as follows:

|  | Positive Results | Negative Results |
| --- | --- | --- |
| Forward flow | 5 | 55 |
| Swab filtration and application per this invention | 0 | 60 |

That all samples were actually negative for Legionella was verified using a conventional ELISA test for Legionella sold by Binax, Inc. Thus, it is demonstrated that with the use of the swab according to this invention, no false positive results were obtained, whereas the same urine samples tested in the forward flow method gave 8.3 percent false positive results.

In subsequent clinical trial testing for 510K approval by the U.S.F.D.A., applicants collected 106 separate urine samples which were stored at 4° C. for a minimum of 16 hours. Each sample was then analyzed using the swab filtration and sample application method of this invention. No false positives were observed.

EXAMPLE 2

E. Coli 0157 Assay

A. Preparation of the Test Device:

The device itself is prepared as in Example 1.

B. Test Strip Preparation and Construction

In the E. coli assay, the test strip is comprised of a first bridge pad, a conjugate pad, a second bridge pad, a nitrocellulose pad and an absorbent as in the Legionella assay.

Gold particles of 45 nm. diameter are conjugated to affinity-purified rabbit anti-E. coli 0157 antibodies. In addition, goat IgG is absorbed to gold particles of 30–50 nm. Both sets of particles are mixed with a drying agent made by dissolving 1.0 percent bovine serum albumin, 0.1 percent Triton X-100, 2.0 percent Tween 20, 6 percent sucrose and 0.02 percent sodium azide in a 5 mM solution of sodium tetraborate in water having a pH of 8.0. Both kinds of particles are embedded into a non-woven polyester pad, which is heated to remove liquid and stored in a low humidity environment pending final assembly of the test device.

The nitrocellulose pad is prepared by embedding affinity-purified rabbit anti-E. coli 0157 antibodies into a first portion of the pad as a capture line and striping rabbit anti-goat IgG on another portion of the pad. The pad is desiccated, blocked and dried again as described in Example 1 and is then stored under low humidity conditions, pending assembly of the test device.

C. Immunoassay Procedure

The procedure is conducted in the same manner as that for Legionella, except that:

1. Reagent A, two drops of which is applied in the manner recited for the Legionella assay, is 0.3 percent Triton X-100 and 0.05 percent ProClin 300 (obtained from Supelco) dissolved in a solution of 0.5 M Tris-HCl of pH 8.0 in water.

2. The sample and control are read after 10 minutes.

D. Advantages of Applying this Invention:

To obtain suitable samples for method testing, a broth was inoculated with a meat sample and the two were incubated overnight. Samples for testing in the forward flow process were then taken by pipette. It was found that large fat particles from the meat often clogged the pipette, while smaller fat particles were carried onto the sample pad and at times appeared to interfere with the assay.

Using the present invention, the swab did not pick up larger fat particles, but the smaller ones which it did pick up were entrapped by the fibers therein so that the liquid sample alone, without fat, was conveyed to the test strip and participated in the assay.

EXAMPLE 3 hCG Assay

A. Test Device Preparation

The test device is prepared in the manner described in Example 1.

B. Test Strip Preparation and Construction

This test strip is generally comprised of a conjugate pad, a nitrocellulose pad and an absorbent pad, arranged in the same order that is specified in Examples 1 and 2. Bridge pads are not needed in this test.

To prepare the conjugate pad, 45 nm gold particles are conjugated to affinity purified monoclonal anti-hCG antibodies. The gold conjugate particles are mixed with a solution of the drying agent referred to in Example II and embedded into a glass fiber conjugate pad. The pad is then treated as in Examples 1 and 2 and stored in a low humidity environment pending use in a test device.

The nitrocellulose pad is treated by embedding affinity purified goat anti-hCG antibodies into a first portion of the pad to form a capture line. In a second portion of the pad, goat anti-mouse IgG is striped on as a control line.

The nitrocellulose pad is dried, blocked and dried again as described in Examples 1 and 2. It is then stored in a low humidity environment pending use in a test device.

C. Immunoassay Procedure

The procedure is the same as that described in Example 1 except that (a) Reagent A is not used, and (b) the sample is delivered directly from the swab well to the conjugate pad. Although the samples tested were from a previously collected and stored urine pool, in actual practice the sample is preferably obtained by holding the swab in the patient's urine stream.

D. Results

As is well-known, the hCG immunoassay test is a pregnancy test and is very often sold for home use. It has suffered heretofore from the fact that the test devices have themselves been constructed to be held in the patient's urine stream, with the result that inclusion of solid, semisolid and/or colloidal particles in the test sample has at times adversely affected the results. The filtering ability of the swab obviates this problem because particles adhere to the swab and do not pass into the test compartment at all.

The hCG test as so conducted was shown to be rapid and highly sensitive in a series of tests conducted as follows:

From a urine pool which contained a high proportion of sediment a series of dilutions were made so that samples containing hCG levels of 300,000, 30,000, 3,000, 300, 30, 3 and 0 mIU/mL were obtained. Multiple assay tests were conducted by first immersing the swabs according to this invention in each of these samples and then proceeding to apply the sample collected by each swab to a device as described in the Example, and then following the balance of the procedure described in this Example. The results, obtained on three assays per dilution, are summarized in Table I:

| Sample (mIU/mL) | Results | Time to Visualize Results |
| --- | --- | --- |
| 0 | Negative | Negative >30 minutes |
| 3 | Positive | ~5 minutes |
| 30 | Positive | ~75 seconds |
| 300 | Positive | ~30 seconds |
| 3,000 | Positive | <30 seconds |
| 30,000 | Positive | <30 seconds |
| 300,000 | Positive | <30 seconds |

In the Examples 1–3, preferred materials for components and ingredients of the test device have generally been specified. Other components and materials, however, may suitably be utilized in lieu of those specified. Thus, for example, gold particles useful in the conjugates may be within the range of 1 to 100 nm, preferably 15–60 nm and most preferably, between 30 and 50 nm. In lieu of gold particles, it is to be understood that any type of label and any type of detection system that produces visible color at the capture line of a test device can be employed.

Useful drying agents include, in addition to those mentioned in the examples, (1) a solution of 1.0 percent bovine serum, 0.1 percent Triton X-100, 2.0 percent Tween-20, 6.0 percent sucrose and 0.02 percent of sodium azide in 5 mM of aqueous sodium tetraborate of pH 8.0, (2) a solution of 4.5 percent sucrose, 1.0 percent Tween-20 and 3 mg./mL of rabbit IgG in aqueous 1.5 M tris-HCl of pH 7.8 and (3) a solution of 1.0 percent bovine serum albumin, 0.1 percent Triton X-100, 2.0 percent Tween-20, 6.0 percent sucrose, 0.02 percent sodium azide and 3/mg/mL rabbit IgG in aqueous 5 mM sodium tetraborate.

While the most preferred conjugate pad is nonwoven polyester from Hollingsworth & Vose, No. 7303, glass fiber is also a preferred material and cellulose, nylon and polypropylene supports from Millipore, Whatman, Ahlstrom, Spectral, Pall-Gelman and others have been found to be acceptable.

In lieu of the blocking agent specified in the examples, polymers such as polyvinyl alcohol and polyvinyl pyrolidine and proteinaceous materials such as serum albumin, gelatin, nonfat dry milk, caesium and immunoglobulin may be used. Blocking agents are preferably sprayed on the nitrocellulose pad, but they may be applied by an immersion method.

Drying of the test strip and components thereof may be affected at temperatures from ambient to 100° C., but those within the range of 30 to 60° C. are preferred. Vacuum and freeze-drying (i.e., lyophilization) methods can also be alternatively employed.

The bridge pads may be of glass fiber rather than the cellulose specified in the Examples. Also suitable are polyester, nylon and polypropylene from the suppliers listed above with respect to the conjugate pad.

Reagent A compositions found suitable in addition to those specified include (1) a solution of 1.0 percent Tween-20, 1.0 percent Triton X-100 and 2.0 percent zwitterionic detergent in aqueous 0.2 M Tris-HCl of pH 8.0, (2) a solution of 0.5 percent Tween-20 and 0.05 percent sodium azide in aqueous 0.05 M Tris-HCl of pH 8.1 and (3) a solution of 0.3 percent Triton X-100 and 0.05 percent Pro Clin 300 in aqueous 0.2 M potassium phosphate of pH 7.2.

The most preferred swab material is fibrous Dacron polyester. Other preferred materials are loose, fibrous cotton and other cellulosic materials and various hydrophilic and hydrophobic foamed materials readily available on the market. It is to be understood that almost any fibrous material wettable by aqueous liquids and almost any open-cell type sponge or foamed material that is not soluble in aqueous media is suitable swab material.

In every case, those skilled in the art will recognize that other materials, ingredients or specific process steps not mentioned herein can also be substituted for those specifically recommended. A wealth of literature, both patent and non-patent, discusses the design and construction of reliable, one-time-use, disposable immunoassay test devices and it is not intended that the present invention should be limited with respect to the use in such devices of the swab according to this invention as herein described and exemplified except to the extent that the following claims may limit such use. Other assay devices, including devices for receptor and test probe assays are also known in the art and it is not intended to limit the use of the swab according to this invention in such assays except insofar as the following claims may do so.

We claim:

1. In a lateral flow assay for detecting, with or without quantifying, a dissolved component of a liquid test sample, which sample is obtained from a pool or flowing stream of liquid which also contains colloidal, semisolid and/or solid substances that, if contained in or carried with the liquid test sample, may interfere with, obscure or otherwise undesirably affect the result obtained, which assay is effected in a lateral flow test device that comprises a test strip having (i) a sample receiving site and (ii) a flow path positioned so that it directly contacts or is adapted to be placed in direct contact with the sample receiving site, along which flow path the liquid test sample, upon contact therewith, flows laterally by capillary action, wicking, sorption or another mechanism capable of promoting or inducing lateral liquid flow, the improvement which comprises (1) providing a flow path free of the presence of filter means and (2) in lieu of filtering the test sample prior to or at any stage of the assay, conducting a preassay procedure enabling delivery of only the liquid test sample directly to the sample receiving site in a condition free of the aforementioned colloidal, semisolid and/or solid substances, which procedure consists of:

(a) providing a swab firmly affixed to a handle, which swab is a sorbent for liquid and is also capable of entrapping or otherwise isolating from the sorbed liquid any colloidal, semisolid and/or solid substances that are present in the original pool or flowing stream of liquid, which swab is formed from a fibrous material or a foamed pore material selected from among resins, rubbers and sponges;

(b) immersing the swab in a pool or a flowing stream of liquid containing colloidal, semisolid and/or solid substances for a period of time sufficient to enable thorough wetting of the swab;

(c) removing the wetted swab from the pool or flowing stream of liquid containing colloidal, semisolid and/or solid substances; and (d) bringing the wetted swab into contact with the sample receiving site of the test strip of the test device and expelling from the swab its sorbed liquid, which is the liquid test sample, directly on the sample receiving site while retaining any colloidal, semisolid and/or solid substances picked up by the swab in step (b) hereof on the swab.

2. The process of claim 1 in which the swab is a fibrous material comprising a fibrous cellulosic material or fibrous polyester.

3. The process of claim 1 in which the assay is an immunoassay.

4. The process of claim 3 in which the test device is an immunochromatographic device.

5. The process of claim 1 in which the assay is a molecular probe assay.

6. The process of claim 1 in which the assay is a receptor assay.

7. In a kit for conducting an assay for a pre-selected dissolved component of a liquid containing undissolved colloidal, semisolid and/or solid substances which kit comprises at least one test device as set forth in claim 1, the improvement which comprises providing at least one swab as set forth in claim 1 for each test device present, each of said swabs being of substantially uniform size and composition, whereby they are each able to deliver essentially the same volume of liquid sample to the test device when utilized in the process of claim 1.

8. The process of claim 1 in which the pool or flowing stream of liquid from which the liquid test sample is obtained and which contains colloidal, semisolid and/or solid substances is urine, blood, lymph, lacteal fluid or another fluid of mammalian origin.

9. The process of claim 8 in which the pool or flowing stream of liquid is a dilution of urine, blood, lymph, lacteal fluid or another fluid of mammalian origin.

10. The process of claim 1 in which the pool or flowing stream of liquid from which the liquid test sample is obtained is an inoculated bacterial medium or a dilution thereof.

11. The process of claim 1 in which the pool or flowing stream of liquid from which the liquid test sample is obtained is groundwater.

12. The process of claim 1 in which the pool or flowing stream of liquid from which the liquid test sample is obtained is selected from among sea water, surface water, heating venting or air conditioning system water, waste water and other aqueous-based media.

* * * * *